United States Patent [19]

DeLuca et al.

[11] 4,202,829
[45] May 13, 1980

[54] PROCESS FOR PREPARING 1α-HYDROXYLATED COMPOUNDS

[75] Inventors: Hector F. DeLuca; Heinrich K. Schnoes; David E. Hamer, all of Madison; Herbert E. Paaren, Verona, all of Wis.

[73] Assignee: Wisconsin Alumni Research Foundation, Madison, Wis.

[21] Appl. No.: 968,738

[22] Filed: Dec. 13, 1978

Related U.S. Application Data

[63] Continuation-in-part of Ser. No. 867,161, Jan. 5, 1978, abandoned.

[51] Int. Cl.² .............................................. C07J 9/00
[52] U.S. Cl. ................................................... 260/397.2
[58] Field of Search ...................................... 260/397.2

[56] References Cited

PUBLICATIONS

"*Steroids*", (Aug. 1977), vol. 30, No. 2, pp. 193–200.

*Primary Examiner*—Elbert L. Roberts
*Attorney, Agent, or Firm*—Howard W. Bremer

[57] ABSTRACT

A method for directly introducing an oxygen function at carbon 1 of the vitamin D molecule or precursors of derivatives thereof which comprises subjecting such molecules to allylic oxidation utilizing selenium dioxide as the oxidizing agent.

11 Claims, No Drawings

PROCESS FOR PREPARING 1α-HYDROXYLATED COMPOUNDS

The invention described herein was made in the course of work under a grant or award from the Department of Health, Education and Welfare.

This application is a continuation in part of co-pending application Ser. No. 867,161, filed Jan. 5, 1978. now abandoned.

This invention relates to a method for preparing compounds having vitamin D-like activity.

More specifically, this invention relates to a method for preparing compounds having vitamin D-like activity which contain an oxygen function at carbon 1 in the molecule.

Still more specifically, this invention relates to a method for preparing 1α-hydroxylated compounds which are characterized by vitamin D-like activity.

It is well known that the D vitamins exhibit certain biological effects, such as stimulation of intestinal calcium absorption, stimulation of bone mineral resorption and the prevention of rickets. It is also now well known that such biological activity is dependent upon these vitamins being altered in vivo, i.e., metabolized, to hydroxylated derivatives. For example, current evidence indicates that 1α,25-dihydroxyvitamin $D_3$ is the in vivo active form of vitamin $D_3$ and is the compound responsible for the aforementioned biological effects.

The synthetic 1α-hydroxyvitamin D analogs, such as 1α-hydroxyvitamin $D_3$, also exhibit pronounced biological potency and such compounds as well as the natural metabolites show great promise as agents for the treatment of a variety of calcium metabolism and bone disorders, such as osteodystrophy, osteomalacia and osteoporosis.

Since 1α-hydroxylation is an essential element in imparting biological activity to the vitamin D compounds and their derivatives there has been increasing interest in methods for chemically accomplishing such hydroxylation. Except for one suggested method for the total synthesis of 1α-hydroxyvitamin $D_3$ (Lythgoe et al, J. Chem. Soc., Perkin Trans I, p. 2654 (1974) all syntheses of 1α-hydroxylated vitamin D compounds involve the preparation of a 1α-hydroxylated steroid, from which, after conversion to the corresponding 1α-hydroxy-5,7-diene sterol derivative, the desired vitamin D compound is obtained by well known photochemical methods. Thus, available syntheses are multistep processes and in most cases are inefficient and laborious.

A new method for introducing a hydroxyl group at the carbon 1 (C-1) position in the vitamin D or vitamin D derivative molecule has now been found which in concept and execution differs radically from existing syntheses. This method, which will be more fully described hereinafter, provides for the direct introduction of an oxygen function at C-1 by allylic oxidation.

More specifically, the method of this invention comprises preparing compounds having the formula

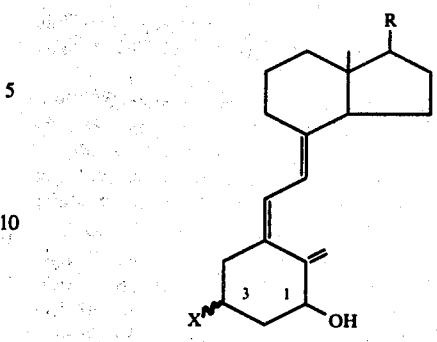

by subjecting compounds having the formulae

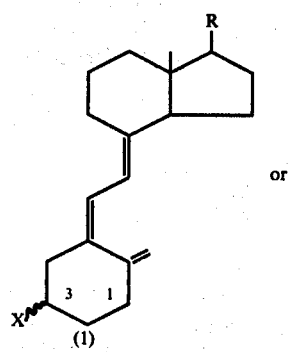

or

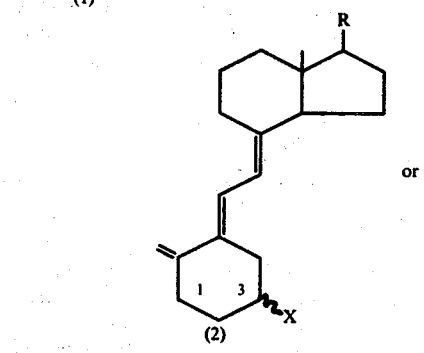

or

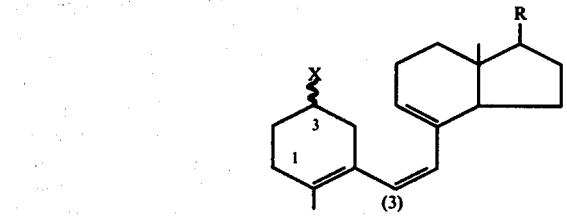

where R is selected from the group consisting of a substituted or unsubstituted cholesterol or ergosterol said chain group, and X is selected from the group consisting of hydrogen, hydroxy, O-lower alkyl, O-lower acyl, O-aromatic acyl and fluorine to allylic oxidation.

Where the starting material has the 5,6-cis-triene chromophore (as in formula (1) above), the allylic oxidation process yields the desired 1-hydroxylated vitamin D compound directly. Where the 5,6-trans form of the vitamin D-like molecule (formula (2) above) is used as the starting material the allylic oxidation product is subsequently subjected to photochemical isomerization to yield the desired 5,6-cis-1-hydroxylated vitamin D compound. Where the previtamin D compound (formula (3) above) is used as starting material the allylic oxidation product is subsequently subjected to thermal isomerization to produce the desired 1-hydroxylated vitamin D compound.

In the formulae shown in this specification and in the claims a wavy line to substituent X indicates that the substituent can be in the α or β stereoisomeric form. Wherever in this specification and in the claims the word "lower" is used as a modifier of alkyl or acyl it is intended to identify a hydrocarbon chain having from about 1 to 4 carbon atoms and can be either a straight chain or branched chain configuration. Specific examples of such hydrocarbon chains are: methyl, ethyl, propyl, butyl, isopropyl, isobutyl or t-butyl, and formyl, acetyl, propionyl, or butyryl. The word "aromatic acyl" as used herein and in the claims is meant to identify a benzoyl group or a substituted benzoyl group such as nitrobenzoyl or dinitrobenzoyl.

In the foregoing formulae, R is preferably, a cholesterol-type side chain of the formula

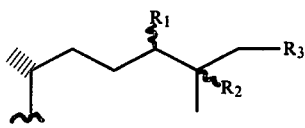

wherein each of $R_1$, $R_2$ and $R_3$ are selected from the group consisting of hydrogen, hydroxy, lower alkyl (e.g. methyl, ethyl), O-lower alkyl, O-lower acyl, O-aromatic acyl and fluorine,
or an ergosterol-type side chain of the formula

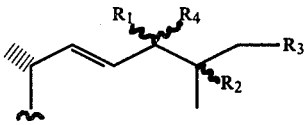

wherein each of $R_1$, $R_2$, and $R_3$ are selected from the group consisting of hydrogen, hydroxy, lower alkyl (e.g. methyl, ethyl), O-lower alkyl, O-lower acyl, O-aromatic acyl and fluorine and wherein $R_4$ is hydrogen or lower alkyl. The wavy lines to substituents $R_1$, $R_2$ and $R_4$ indicate that these substituents can be in either the α or β-stereoisomeric form.

Of particular interest is the application of the allylic oxidation process to starting materials where X is hydroxy and where R represents a cholesterol-type sidechain in which $R_1$, $R_2$, and $R_3$ are hydrogen or where $R_1$ and $R_3$ are hydrogen and $R_2$ is hydroxy. Other preferred starting materials include compounds where X is hydroxy and where R represents an ergosterol-type side chain in which $R_1$, $R_2$ and $R_3$ are hydrogen, or in which $R_1$ and $R_3$ are hydrogen and $R_2$ is hydroxy and where $R_4$ is methyl having the stereochemical configuration as in ergosterol.

The process of this invention involves the introduction of a hydroxyfunction at carbon 1 of the starting materials of formula (1), (2) or (3) above by allylic oxidation. The general term "allylic oxidation" refers to the oxidation of an olefin at the allylic position and the introduction of oxygen at that position (Rabjohn, Organic Reactions, Vol. 24, p. 266 1976; House, Modern Synthetic Reactions, 2nd Ed., p. 335, W. A. Benjamin Publishers, In., Menlo Park, Cal. 1972). Such oxidations can be accomplished by a number of reagents of which $SeO_2$ is a well-known example. However, such oxidations have not previously been attempted using vitamin D compounds or their derivatives as the starting olefin, presumably because of the well-known sensitivity of the vitamin D triene structure, which would be expected to lead to decomposition of the molecule when subjected to oxidizing conditions. Furthermore the presence of at least four allylic carbons in starting materials of formulae (1), (2) or (3) above would be expected to lead to a great multiplicity of allylic oxidation products in addition to the products that might result from rearrangement or decomposition of the triene system under allylic oxidation conditions.

We have now found, however, that under suitable conditions, vitamin D starting materials of formulae (1), (2) and (3) above can be oxidized specifically at the C-1-allylic position to yield the corresponding 1-hydroxylated compounds. The allylic oxidation of vitamin D compounds is preferably carried out in a suitable solvent with selenium dioxide as oxidizing agent. The reaction is conveniently conducted in the presence of a hydroperoxide, e.g. hydrogen peroxide or an alkyl hydroperoxide, e.g. t-butylhydroperoxide (Umbreit and Sharpless et al, J. Am. Chem. Soc. 99, 5526–5528, 1977) but the presence of such material is not necessary to obtain the desired product. Suitable solvents include chlorocarbon solvents, e.g. dichloromethane, chloroform, or pyridine, or mixtures of these solvents. When the oxidation is conducted in the absence of a hydroperoxide, hydroxylic solvents, e.g. methanol, ethanol, t-butyl alcohol, or mixtures of hydroxylic and chlorocarbon solvents are preferred. Oxidation can be effected at temperatures ranging from, about −30° to room temperature, although, as a practical matter, temperatures in the range from 0° to about 25° C. are preferred. Reaction times of 2 to 24 hours are appropriate, depending upon the solvent, the temperature and the starting material chosen. It is preferred that the reaction be conducted under a nitrogen atmosphere to avoid air oxidation.

Suitable starting materials for the allylic oxidation process are vitamin D compounds of general formula (1) above, or 5,6-trans-vitamin D compounds of general formula (2) above, or previtamin D compounds of general formula (3) above. With compounds of the general formula (1) above the process of this invention can be readily depicted as follows:

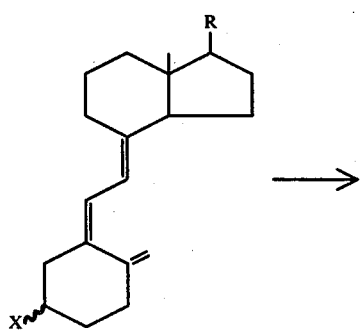

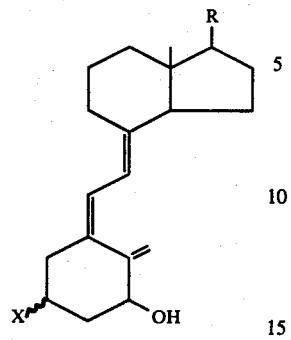

where R and X have the designation set out hereinbefore. The resulting 1α-hydroxyvitamin D compound can be recovered from the reaction mixture by chromatographic methods, such as thin-layer chromatography or highpressure liquid chromatography. The reaction mixture also contains the corresponding 1β-hydroxyvitamin D compound, as well as the 1α-hydroxy-5,6-trans-vitamin D compound and the 1β-hydroxy-5,6-trans-vitamin D compound, all of which, if desired, can be recovered in pure forms by chromatographic methods. The conversion depicted above thus represents a direct 1-step method for the preparation of 1-hydroxylated vitamin D compounds or of 1-hydroxylated-5,6-trans-vitamin D compounds.

Where the starting material is a 5,6-trans-vitamin D compound (as in formula (2) above) the process schematic can be depicted as follows:

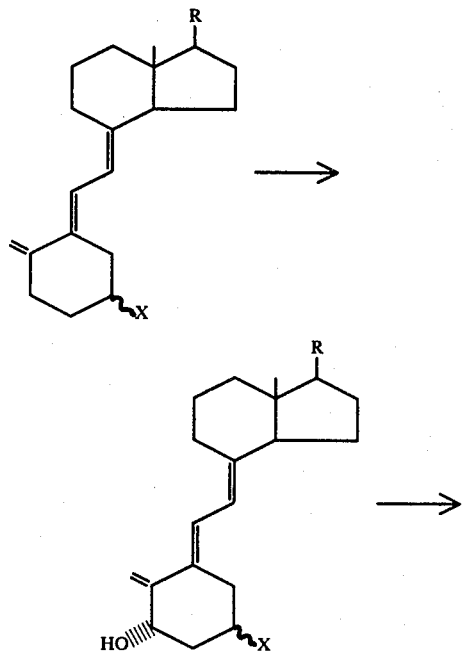

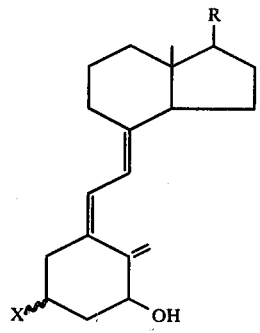

here R and X have the designations given above. Allylic oxidation of the 5,6-trans-vitamin D starting material results in a product mixture containing the 1α-hydroxy and the 1β-hydroxy-product, from which the 1α-hydroxy-5,6-trans epimer illustrated in the above schematic can be recovered by chromatography. This 1α-hydroxylated 5,6-trans compound can be converted to the 1α-hydroxyvitamin D structure (5,6-cis) by known methods, e.g. irradiation with ultraviolet light as described by Inhoffen et al. (Chem. Ber. 90, 2544–2553, 1957). From the reaction mixture resulting from allylic oxidation, the 1β-hydroxy-5,6-trans-vitamin D compound can also be isolated by chromatographic methods, if desired. A noteworthy advantage of the use of 5,6-trans-compounds of general structure (2) as starting materials for the process of this invention is that they are more reactive towards allylic oxidation and yield the corresponding 1-hydroxylated product in higher yield.

When the starting material is a previtamin D compound (of formula (3) above) the process schematic is depicted as follows:

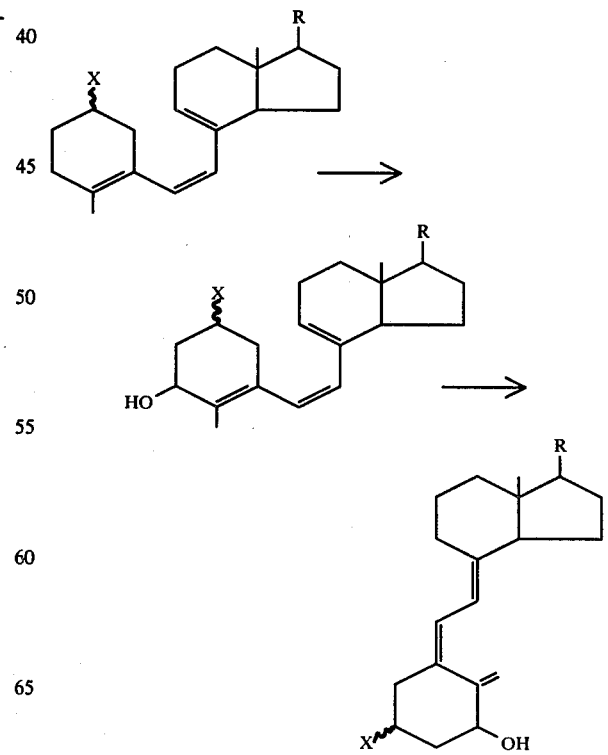

where R and X have the designations set out above. From the mixture resulting from allylic oxidation of the previtamin D starting material the desired 1α-hydroxy-previtamin D compound is isolated by chromatographic methods, and then subjected to thermal isomerization by heating the previtamin compound to about 70° C. in a hydrocarbon or alcoholic solvent, (e.g. DeLuca et al. U.S. Pat. No. 3,907,843) and recovering the corresponding 1α-hydroxylated vitamin D compound shown in the above schematic. Alternatively, the reaction mixture resulting from allylic oxidation can be heated directly to accomplish the isomerization depicted, followed by isolation of the desired 1α-hydroxyvitamin D compound. The thermal isomzerization in both instances can be carried out over a relatively broad range of temperatures, e.g. from about 20° C. to about 90° C. as is well known in the art, it being understood that the isomerization proceeds more slowly at the lower temperatures. The allylic oxidation product mixture of a previtamin D starting material also contains the corresponding 1β-hydroxy-previtamin D product which, if desired, can be readily recovered from the mixture by chromatographic methods.

The allylic oxidation process of this invention provides a new route to 1-hydroxylated vitamin D compounds. A particular advantage of this process over previously known methods is it directness, providing 1-hydroxyvitamin D compounds in one or two simple steps depending on the choice of starting material. A further advantage of the process is its generality. Starting materials of formulae (1), (2) or (3) above, bearing a broad range of substituents at C-3 and/or in the side chain group R, are suitable for this process. Thus, for example, oxidation of vitamin $D_3$ yields 1α-hydroxyvitamin $D_3$ and oxidation of 25-hydroxyvitamin $D_3$ yields 1α,25-dihydroxyvitamin $D_3$ in one step. Similarly, oxidation of vitamin $D_2$ provides 1α-hydroxyvitamin $D_2$ and 1α,25-dihydroxyvitamin $D_2$ can be obtained by the method of this invention from 25-hydroxyvitamin $D_2$. In like manner, oxidation of 5,6-trans-vitamin $D_3$ or 5,6-trans-vitamin $D_2$ readily affords the corresponding 1α-hydroxy-5,6-trans-vitamin D compounds, which can, of course, be converted to 1α-hydroxyvitamin $D_3$ or 1α-hydroxyvitamin $D_2$ by known photochemical methods. The same end compounds can also be obtained from the respective previtamin D structures by allylic oxidation and subsequent thermal isomerization.

The following specific examples will serve to better illustrate the present invention but are not to be considered limiting of the scope of the invention, alteration of various conditions and the use of various alternative solvents and separation techniques employed being well within the purview of the art.

It will be evident from the examples that although vitamin D-like compounds bearing free hydroxy functions are suitable starting materials for the process of this invention, the corresponding O-protected derivatives can also be used. For example, when oxidized as described herein, vitamin $D_3$-3-benzoate yields 1α-hydroxyvitamin $D_3$-3-benzoate, and 25-hydroxyvitamin $D_3$-3-acetate yields 1α,25-dihydroxyvitamin $D_3$-acetate. Similarly, O-lower acyl, or O-aromatic acyl-5,6-trans-vitamin D compounds, or the corresponding previtamin D compounds, are also effective substrates for the present allylic oxidation process. O-acylated products resulting from the oxidation of such starting materials can, of course, be converted to the corresponding hydroxy products by hydrolysis under basic conditions (e.g. NaOH, aqueous methanol 70° C.) as is well known in the art.

EXAMPLE 1

Synthesis of 1α-Hydroxyvitamin $D_3$ from Vitamin $D_3$: To a cooled solution of 81.5 mg (0.21 mmol) of vitamin $D_3$ in 1.5 ml of dichloromethane 60 μl (2.0 equivalents) of 70% tert-butyl hydroperoxide is added followed by 145 μl (0.25 equivalent) of a 0.36 M solution of selenium dioxide in tertbutyl alcohol. The solution is stirred in the dark at 0° C. under a nitrogen atmosphere for 6.5 hr. The reaction mixture is diluted with 4 ml of dichloromethane, after which 10 ml of a 10% sodium hydroxide solution is added. The resulting two phase mixture is transferred to a 50 ml separatory funnel and further diluted with 20 ml of dichloromethane and 10 ml of a 10% sodium hydroxide solution to help clear the resultant emulsion. After phase separation, the organic layer is washed with four-8 ml aliquots of water, dried (MgSO$_4$), filtered, and evaporated. The crude product (77.9 mg) is chromatographed on a silica gel F-254 TLC plate (thin layer chromatography plate marketed by E. Merck & Co.) (20×20 cm-500 μm layer thickness) with 10% ethyl acetate-ether (four elutions). A band with $R_f$ similar to that of an authentic sample of 1α-hydroxyvitamin $D_3$ is removed and the isolated material is rechromatographed on a similar TLC plate using ether as the developing solvent (four elutions). The lower of the two resulting bands is removed and the isolated material rechromatographed as above using 2.5% methanol-chloroform (four elutions). The lowest of the three resulting bands is removed and the isolated material rechromatographed a second time with 2.5% methanol-chloroform (six elutions) yielding 226 μg (0.27% yield—quantitation by uv spectroscopy) of a colorless oil exhibiting the following physico-chemical characteristics: uv (EtOH) $\lambda_{max}$ 265 nm, $\lambda_{min}$ 224 nm; nmr (270 MHz, CDCl$_3$) δ 6.38 and 6.09 (AB, J=11.5 Hz, 2H, C-6,7), 5.36 (t, J=1.4 Hz, 1H, C-19), 5.06 (m,w$_{1/w}$=4.28 Hz, 1H, C-19), 4.51 (br, m, 1H, C-1), 4.33 (br m, 1H, C3), 0.92 (d, J=6 Hz, 3H, C-21), 0.86 (d, J=6.5 Hz, 6H, C-26,27), 0.54 (s, 3H, C-18); mass spectrum (70 eV) m/e (relative intensity) 400 (M+, 19), 382 (M-H$_2$O, 35), 364 (M-2H$_2$O, 19), 152 (28), and 134 (95).

EXAMPLE 2

Synthesis of 1α,25-Dihydroxyvitamin $D_3$ from 25-Hydroxyvitamin $D_3$: To a stirred, cooled solution of 99.5 mg (0.25 mmol) of 25-hydroxyvitamin $D_3$ 70 μl (2 equivalents) of 70% tert-butyl hydroperoxide is added dropwise followed by 360 μl (0.5 equivalent) of a 0.36 M solution of selenium dioxide in tert-butyl alcohol. The solution is stirred in the dark at 0° C. under a nitrogen atmosphere for 320 min. The reaction mixture is diluted with 5 ml of dichloromethane and 4 ml of a 10% sodium hydroxide solution was added. The mixture is transferred to a 50 ml separatory funnel and diluted with 10 ml of dichloromethane and 5 ml of water. After phase separation the organic layer is washed with two-5 ml aliquots of water, dried (sodium sulphate), filtered, and evaporated. The crude product (62.5 mg) is chromatographed on a silica gel F-254 TLC plate (20×20 cm-500 μm layer thickness) with 50% ethyl acetate-hexane (five elutions). A bnad with $R_f$ similar to that of a standard sample of 1α,25-dihydroxyvitamin $D_3$ is removed and the isolated material rechromatographed on a similar TLC plate using 5% methanol-chloroform as the developing solvent (six elutions). The lower of the two resulting bands is removed and the isolated material chromatographed by reverse-phase, high-pressure liquid chromatography (Zorbax ODS (a column octadecylsilane bonded to a fine grained silica gel, for high pressure liquid chromatography marketed by the DuPont Company), 25% water-methanol, flow rate 1 ml/min). Fractions containing the slower eluting ($t_r$=55.5 min) of two components are pooled and evaporated yielding 42 μg (0.04% yield—quantitation by uv spectroscopy) of a colorless oil having the following physico-chemical characteristics: uv (EtOH) $\lambda_{max}$ 264 nm, $\lambda_{min}$ 226 nm; nmr (270 MHz, $CDCl_3$) δ 6.37 and 6.01 (AB, J=11.4 Hz, 2H, C-6,7), 5.33 (m, 1H, C-19), 5.01 (m, 1H, C-19), 4.44 (br m, 1H, C-1), 4.24 (br m, 1H, C-3), 1.22 (s, 6H, C-26,27), 0.94 (d, J=6.4 Hz, 3H, C-21), and 0.55 (s, 3H, C-18); mass spectrum (70 eV) m/e (relative intensity) 416 ($M^+$, 5), 398 (M—$H_2O$, 13), 380 (M—$2H_2O$, 11), 365 (4), 152 (34), and 134 (73). This product is identical with authentic 1α,25-dihydroxyvitamin $D_3$.

EXAMPLE 3

Synthesis of 5,6-trans-1β-Hydroxyvitamin $D_3$ from Vitamin $D_3$: A 25 ml round-bottomed flask is charged with 11.4 mg (0.10 mmol) of selenium dioxide, 6 ml of dichloromethane, 50 μl (0.50 mmol) of t-butylhydroperoxide (dried over sodium sulfate) and 50 μl of pyridine. The mixture is stirred at room temperature for 0.5 hr to allow the selenium dioxide to dissolve. The solution is cooled in an ice-water bath then a solution of 11.4 mg (0.03 mmol) of vitamin $D_3$ in 2 ml of dichloromethane is added. The reaction mixture is stirred at 0° for 4.5 hr then diluted with 10 ml of 10% aqueous sodium hydroxide and 50 ml of ethyl acetate. The two phases are separated and the organic layer washed with 10% aqueous sodium hydroxide (10 ml, 2X) and water (10 ml, 4X). The organic layer is evaporated yielding 11.8 mg of crude product which is chromatographed in a multiple development mode (Perry et al., Anal. Chem. 47, 65A, 1975) on a silica gel F-254 TLC plate (20×20 cm, 500 μm layer thickness) using 5% methanol in chloroform as the developing solvent. A band with $R_f$ similar to that of a known sample of trans-1β-hydroxyvitamin $D_3$ is removed and the silica gel is extracted with ethyl acetate (1 ml, 2X) then chloroform (1 ml, 2X). Evaporation of the solvents yields 2.0 mg (17% yield) of a colorless oil characterized as 5,6-trans-1β-hydroxyvitamin $D_3$ by the following spectroscopic and chromatographic data: uv (EtOH) $\lambda_{max}$ 268 nm; nmr (270 MHz, $CDCl_3$) δ 6.64 and 5.90 (AB, J= 11.4 Hz, 2H, C-6,7), 5.12 (d, J=1.5 Hz, 1H, C-19), 4.96 (bs, 1H, C-19), 4.38 (br m, 1H, C-1), 4.11 (br m, 1H, C-3), 0.92 (d, J=6 Hz, 3H, C-21), 0.87 (d, J=6.5 Hz, 6H, C-26,27), 0.57 (s, 3H, C-18); mass spectrum (70 eV) m/e (relative intensity) 400 ($M^+$, 35), 382 (M—$H_2O$, 8), 152 (100), 135 (68), and 134 (60); the sample cochromatographs with a known sample of this compound (prepared by iodine catalyzed isomerization of 1β-hydroxyvitamin $D_3$) on silica gel TLC (5% methanol in chloroform).

EXAMPLE 4

Synthesis of 5,6-trans-1α-Hydroxyvitamin $D_3$ and 5,6-trans-1β-Hydroxy vitamin $D_3$ from 5,6-trans-Vitamin $D_3$: To a 10 ml round-bottomed flask equipped with 1 cm stirring bar is added 8.3 mg (0.07 mmol) of selenium dioxide followed by 200 μl of dichloromethane. To the suspension is added 25 μl of dried t-butylhydroperoxide followed by 200 μl of pyridine. The resulting solution is stirred at room temperature for 1 hr then cooled to 0°. To the cooled solution 37.6 mg (0.10 mmol) of 5,6-trans-vitamin $D_3$ is added followed immediately by 200 μl of dichloromethane. The reaction mixture is stirred at 0° under nitrogen for 280 min then worked up by pouring onto a mixture of 12 ml of ether and 8 ml of 10% aqueous sodium hydroxide. After phase separation the ether layer is washed with 10% sodium hydroxide (5 ml, 2X) and water (5 ml, 6X). After evaporation of the solvent 25.3 mg of crude product is recovered. The crude product is chromatographed in a multiple development mode on a silica gel F-254 TLC plate (20×20 cm, 500 μm layer thickness) using 5% methanol in chloroform as the developing solvent. A band with $R_f$ similar to that of a known sample of trans-1α-hydroxyvitamin $D_3$ is removed and extracted with ethyl acetate and chloroform. Evaporation of the solvents yields 4 mg (10% yield) of colorless oil characterized as trans-1α-hydroxyvitamin $D_3$ by the following spectroscopic and chromatographic data: uv (EtOH) $\lambda_{max}$ 272 nm; nmr (270 MHz, $CDCl_3$) δ 6.58 and 5.88 (AB, J=11 Hz, 2H, C-6,7), 5.12 (d, J=1.5 Hz, 1H, C-19), 4.97 (bs, 1H, C-19), 4.50 (br m, 1H, C-1), 4.24 (br m, 1H, C-3), 0.92 (d, J=6 Hz, 3H, C-21), 0.88 (d, J=6 Hz, 6H, C-26,27), 0.56 (s, 3H, C-18); mass spectrum (70 eV) m/e (relative intensity) 400 ($M^+$, 13), 382 (17-$H_2O$, 10), 364 (M—$2H_2O$, 4), 152 (36), and 134 (100); the sample cochromatographs with a known sample of this compound (prepared by iodine catalyzed isomerization of 1α-hydroxyvitamin $D_3$) on silica gel TLC (5% methanol in chloroform).

A second band is removed from the TLC plate and the silica gel is extracted with ethyl acetate (1 ml, 2X) then chloroform (1 ml, 2X). Evaporation of the solvents yields 1.6 mg (4% yield) of a colorless oil which exhibits the following physico-chemical characteristics: uv (EtOH) $\lambda_{max}$ 268 nm; nmr (270 MHz, $CDCl_3$) δ 6.64 and 5.90 (AB, J=11.5 Hz, 2H, C-6,7), 5.12 (d, J=1.5 Hz, 1H, C-19), 4.96 (bs, 1H, C-19), 4.38 (br m, 1H, C-1), 4.11 (br m, 1H, C-3), 0.92 (d, J=6 Hz, 3H, C-21), 0.87 (d, J=6.5 Hz, 6H, C-26,27), 0.57 (s, 3H, C-18); mass spectrum (70 eV) m/e (relative intensity) 400 ($M^+$, 22), 382 (M—$H_2O$, 7), 291 (9), 152 (100), 135 (73), and 134 (76); co-migration of this material with an authentic sample of 5,6-trans-1β-hydroxyvitamin $D_3$ on silica gel TLC (2.5% methanol-chloroform) as well as a consideration of the spectroscopic properties of the product establishes the identity of the product as 5,6-trans-1β-hydroxyvitamin $D_3$.

EXAMPLE 5

Synthesis of 5,6-trans-1α,25-Dihydroxyvitamin $D_3$ and 5,6-trans-1β,25-Dihydroxyvitamin $D_3$ from 5,6-trans-25-Hydroxyvitamin $D_3$: A 10 ml round-bottomed flask is charged with 9.8 mg (0.09 mmol) of selenium dioxide and 200 μl of dichloromethane. To the suspension is added 25 μl of dried t-butyl hydroperoxide followed by 200 μl of pyridine. The resulting solution is stirred at room temperature for 0.5 hr. then cooled to 0°. To the cooled solution is added 40.7 mg (0.10 mmol) of 5,6-trans-25-hydroxyvitamin $D_3$ followed immediately by 200 μl of dichloromethane. The reaction is continued at 0° under nitrogen for 190 min. then worked up by pouring onto a mixture of 15 ml of ethyl acetate and 10 ml of 10% aqueous sodium hydroxide. After phase separation the organic layer is washed with 10% aqueous sodium hydroxide (15 ml, 2X) and water (5 ml, 6X).

The crude product is chromatographed on a silica gel F-254 TLC plate (20×20 cm—500 μm layer thickness) in a multiple development mode using 5% methanol in chloroform as the developing solvent. The lower of two bands migrating slower than the starting material is eluted with ethyl acetate and chloroform. Solvent removal yields 3.6 mg (9.6% yield) of 5,6-trans-1α,25-dihydroxyvitamin $D_3$: uv (EtOH) $\lambda_{max}$ 271 nm; mass spectrum (70 eV) m/e (relative intensity) 416 (M+, 4) 398 (M—$H_2O$, 6), 380 (M—2 $H_2O$), 285 (4), 152 (24), and 134 (88); nmr (270 MHz, $CDCl_3$) δ 6.6 and 5.9 (AB, J=11 Hz, 2H, C-6,7), 5.1 (br s, 1H, C-19) 5.0 (br s, 1H, C-19), 4.5 (br m, 1H, C-11, 4.2 (br m, 1H, C-3), 1.2 (s, 6H, C-26,27), 0.95 (d, J=6 Hz, 3H, C-21) and 0.57 (s, 3H, C-18).

A second polar band is eluted from the TLC plate with ethyl acetate (1 ml, 2X) and chloroform (1 ml, 2X). Evaporation of the solvents yields 1.3 mg (3% yield) of 5,6-trans-1β,25-dihydroxyvitamin $D_3$: uv (EtOH) $\lambda_{max}$ 268 nm; mass spectrum (70 eV) m/e (relative intensity) 416 (M+, 12), 398 (M—$H_2O$, 6), 380 (M-2 $H_2$), 4), 152 (85), 135 (88) and 134 (100); nmr (270 MHz, $CDCl_3$) δ 6.6 and 5.9 (AB, J=11.6 Hz, 2H, C-6,7), 5.1 (d, J=1.5 Hz, 1H, C-19), 5.0 (br s, 1H, C-19), 4.4 (t, J=4.5 Hz, 1H, C-1), 4.1 (br m, 1H, C-3), 1.22 (s, 6H, C-26,27), 0.95 (d, J=6 Hz, 3H, C-21), and 0.57 (s, 3H, C-18); the sample cochromatographs with a known sample of this compound (prepared by iodine catalyzed isomerization of 1β,25-dihydroxyvitamin $D_3$) on silica gel TLC (50% ethyl acetate in Skelly B).

EXAMPLE 6

1α-Hydroxyvitamin $D_3$ and 5,6-trans-1α-Hydroxyvitamin $D_3$ from Vitamin $D_3$: To a stirred suspension of 4.8 mg (0.04 mmol) of selenium dioxide in 200 μl of pyridine is added 25 μl of dried tert-butyl hydroperoxide. The resulting solution is stirred under nitrogen at room temperature for 0.5 hr. To the solution a charge of 33.2 mg (0.086 mmol) of vitamin $D_3$ is added followed immediately by 200 μl of pyridine. After 20 hr at room temperature the reaction is worked up by pouring the reaction mixture onto 10 ml of 10% aqueous sodium hydroxide and 20 ml of ethyl acetate. The organic layer is further washed with water (10 ml, 3X) and evaporated. The crude product (30.0 mg) is chromatographed on a silica gel F-254 TLC plate (see above) (20×20 cm—500 μm layer thickness) in a multiple development mode using 5% methanol in chloroform as the developing solvent. A band with $R_f$ similar to that of an authentic sample of 1α-hydroxyvitamin $D_3$ is removed and the isolated material is rechromatographed on a preparative TLC plate made of silica gel (made from equal proportions of silica gel H and silica gel 60PF-254, both products of E. Merck & Co.) (20×20 cm—750 μm layer thickness) in a multiple development mode using 50% ether in chloroform as the developing solvent. The lower of the two resulting bands is removed and the silica gel extracted with ethyl acetate (1 ml, 2X) then chloroform (1 ml, 2X). Evaporation of the solvents yields 175 μg (0.5% yield-quantitation by uv spectroscopy) of a colorless oil shown to be identical with 1α-hydroxyvitamin $D_3$ by comparison of the sample's chromatographic properties and nmr, uv and mass spectra with those of an authentic sample of this compound.

The upper band of material from the second chromatographic plate is removed and the silica gel is extracted with ethyl acetate (1 ml, 2X) and chloroform (1 ml, 2X). Removal of the solvents yields 450 μg (1.4% yield-quantitation by uv spectroscopy) of a colorless oil shown to be 5,6-trans-1α-hydroxyvitamin $D_3$ by direct comparison of uv, mass and nmr spectra with those of authentic samples of this compound.

EXAMPLE 7

1α-Hydroxyvitamin $D_2$ and 5,6-trans-1α-Hydroxyvitamin $D_2$ from Vitamin $D_2$: To a suspension of 6.8 mg (0.06 mmol) of selenium dioxide in 400 μl of pyridine is added 25 μl of dried tert-butyl hydroperoxide. The solution is stirred for 1 hr then 29.7 mg (0.075 mmol) of vitamin $D_2$ is added. After 18.5 hr at room temperature the reaction mixture is poured onto a mixture of 10 ml of 10% aqueous sodium hydroxide and 15 ml of ethyl acetate. The organic layer is washed with water (5 ml, 4X) then evaporated yielding 26.7 mg of crude product. The crude product is chromatographed on a silica gel TLC plate (20×20 cm—750 μm layer thickness) in a multiple development mode using 5% methanol in chloroform as the developing solvent. A band of material with polarity similar to that of a sample of 1α-hydroxyvitamin $D_2$ is removed and the isolated material rechromatographed on a second similar plate using 50% ether in chloroform as the developing solvent. The lower of the two resulting bands is removed and the silica gel extracted with ethyl acetate (1 ml, 2X) then chloroform (1 ml, 2X). Evaporation of the solvents yields 212 μg (0.7% yield—quantitation by uv spectroscopy) of a colorless oil exhibiting the following physical-chemical characteristics: uv (EtOH) $\lambda_{max}$ 265 nm; mass spectrum (70 eV) m/e (relative intensity) 412 (M+, 34) 394 (M—$H_2O$, 50), 376 (M—$2H_2O$, 35), 152 (66), 135 (98), and 134 (100); nmr (270 MHz, $CDCl_3$) δ 6.02 and 6.38 (AB, J=11 Hz, 2M, C-6,7), 5.32 (d, J=1.4 Hz, 1H, C-14), 5.20 (m, 2H, C-22,23), 5.00 (m, 1H, C-19), 4.42 (br m, 1H, C-1), 4.23 (br m, 1H, C-3), 1.02 (d, J=6.6 Hz, 3H, C-28), 0.92 (d, J=6 Hz, 3H, C-21), 0.82 and 0.84 (d, J=4.4 Hz, 6H, C-26,27) and 0.56 (s, 3H, C-18). Direct comparison of these data with those of an authentic sample of this compound confirms the identity of the product as 1α-hydroxyvitamin $D_2$.

Isolation of the material in the upper band of the second TLC plate yields 507 μg (1.6% yield-quantitation by uv spectroscopy) of 5,6-trans-1α-hydroxyvitamin $D_2$ identified by comparison of uv, mass and nmr spectra with those of an authentic sample of this compound.

EXAMPLE 8

1α,24(R),25-Trihydroxyvitamin $D_3$ from 24(R),25-Dihydroxyvitamin $D_3$: To a suspension of 2.1 mg (0.02 mmol) of selenium dioxide in 200 μl of pyridine is added 10 μl of dried tert-butyl hydroperoxide. The solution is stirred at room temperature under nitrogen for 1.5 hr then 7.7 mg (0.019 mmol) of 24(R),25-dihydroxyvitamin $D_3$ is added. After 27 hr at room temperature the reaction mixture is poured onto a mixture of 4 ml of 10% aqueous sodium hydroxide and 6 ml of ethyl acetate. The organic layer is washed with water (2 ml, 4X), then evaporated yielding 6.2 mg of crude product. The crude product is chromatographed on a silica gel TLC plate (20×20 cm—750 μm layer thickness) in a multiple development mode using 7% methanol in chloroform as the developing solvent. A band of material with polarity similar to that of a sample of 1α,24(R),25-trihydroxyvitamin $D_3$ is removed and the isolated material rechromatographed on a second similar plate using 25% chloroform in ether as the developing solvent. A band of material co-migrating with a sample of the desired product is removed and the silica gel extracted with ethyl acetate (1 ml, 2X) then chloroform (1 ml, 2X). Evaporation of the solvents yields 49 μg of 1α,24(R),25-trihydroxyvitamin $D_3$ (0.6% yield—quantitation by uv spectroscopy) identical in all respects to an authentic sample of this compound.

Having thus described the invention what is claimed is:

1. A method for preparing 1α-hydroxylated compounds having the general formulae

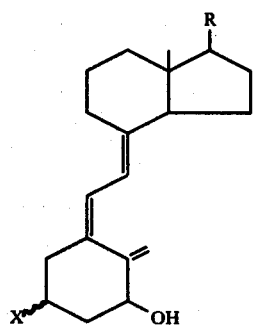

where R is selected from the group consisting of a substituted or unsubstituted cholesterol or ergosterol side chain group, and X is selected from the group consisting of hydrogen, hydroxy, acyl, O-lower alkyl, O-lower acyl, and O-aromatic acyl, which comprises subjecting compounds having the formulae

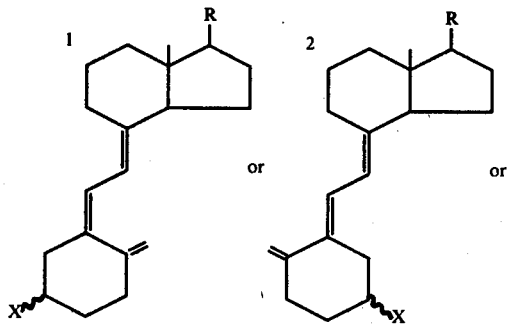

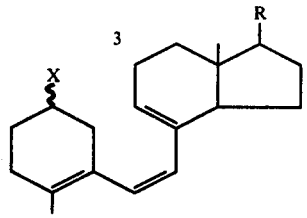

to allylic oxidation, with the proviso that the 1-hydroxylated product of a compound of formula (2) be subsequently subjected to isomerization by irradiation with ultraviolet light and the 1-hydroxylated product of a compound of formula (3) be subsequently subjected to thermal isomerization and recovering the desired 1-hydroxylated product.

2. The method of claim 1 wherein the allylic oxidation is carried out with selenium dioxide as the oxidant.

3. The method of claim 1 wherein the allylic oxidation is carried out with selenium dioxide as the oxidant in the presence of an alkyl hydroperoxide.

4. The method of claim 1 wherein R has the formula

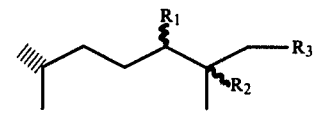

wherein each of $R_1$, $R_2$ and $R_3$ are selected from the group consisting of hydrogen, hydroxy, lower alkyl, O-lower alkyl, O-lower acyl, O-aromatic acyl, and fluorine.

5. The method of claim 4 wherein $R_1$ and $R_3$ are hydrogen and $R_2$ is hydroxy.

6. The method of claim 5 wherein X is hydroxy.

7. The method of claim 4 wherein $R_1$, $R_2$ and $R_3$ are hydrogen and X is hydroxy.

8. The method of claim 1 wherein R has the formula

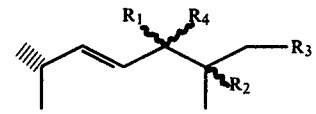

wherein each of $R_1$, $R_2$ and $R_3$ are selected from the group consisting of hydrogen, hydroxy, lower alkyl, O-lower alkyl, O-lower acyl, O-aromatic acyl, and fluorine, and wherein $R_4$ is hydrogen or lower alkyl.

9. The method of claim 8 wherein $R_1$ and $R_3$ are hydrogen, $R_2$ is hydroxy and $R_4$ is methyl.

10. The method of claim 9 wherein X is hydroxyl.

11. The method of claim 8 wherein $R_1$, $R_2$ and $R_3$ are hydrogen, $R_4$ is methyl and X is hydroxyl.

* * * * *